(12) United States Patent
Renner et al.

(10) Patent No.: US 7,662,096 B2
(45) Date of Patent: Feb. 16, 2010

(54) METHOD FOR ASSEMBLING AN ENDOSCOPE

(75) Inventors: Klaus Renner, Liptingen (DE); Steffen Brüsehaber, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 734 days.

(21) Appl. No.: 11/206,694

(22) Filed: Aug. 18, 2005

(65) Prior Publication Data

US 2006/0036132 A1    Feb. 16, 2006

Related U.S. Application Data

(63) Continuation of application No. PCT/EP2004/000766, filed on Jan. 29, 2004.

(30) Foreign Application Priority Data

Feb. 18, 2003    (DE) ................ 103 07 903

(51) Int. Cl.
    *A61B 1/07* (2006.01)
(52) U.S. Cl. .............. 600/182; 600/920; 600/128; 600/130; 385/117
(58) Field of Classification Search .......... 600/920, 600/182, 130, 128; 385/116–118, 106
See application file for complete search history.

(56) References Cited

U.S. PATENT DOCUMENTS

| | | | | |
|---|---|---|---|---|
| 3,496,931 A | * | 2/1970 | Pilling ................... 600/128 |
| 3,699,950 A | * | 10/1972 | Humphrey et al. ........ 600/249 |
| 4,173,392 A | * | 11/1979 | Ekinaka et al. ........... 385/117 |
| 4,483,585 A | * | 11/1984 | Takami .................. 385/115 |
| 4,616,631 A | * | 10/1986 | Takahashi ............... 600/139 |
| 4,652,288 A | * | 3/1987 | Saito ..................... 65/389 |
| 4,706,654 A | * | 11/1987 | Ogiu et al. .............. 600/130 |
| 4,715,105 A | * | 12/1987 | Beaver ................... 29/419.1 |
| 4,782,819 A | * | 11/1988 | Adair .................... 600/109 |
| 4,784,464 A | * | 11/1988 | Ouchi .................... 385/117 |
| 4,813,400 A | * | 3/1989 | Washizuka et al. ........ 600/161 |
| 4,822,154 A | * | 4/1989 | Oxford et al. ............ 359/367 |
| 4,832,003 A | * | 5/1989 | Yabe ..................... 600/109 |
| 4,871,229 A | * | 10/1989 | Tashiro .................. 385/117 |
| 5,041,108 A | * | 8/1991 | Fox et al. ................ 606/7 |
| 5,073,048 A | * | 12/1991 | Adachi et al. ............ 385/115 |
| 5,305,736 A | * | 4/1994 | Ito ....................... 600/109 |
| 5,354,518 A | * | 10/1994 | Okada et al. ............. 264/1.25 |

(Continued)

FOREIGN PATENT DOCUMENTS

DE    1 869 483    3/1963

(Continued)

OTHER PUBLICATIONS

International Search Report (PCT, 8 pages, Jul. 15, 2004).

*Primary Examiner*—John P Leubecker
(74) *Attorney, Agent, or Firm*—St. Onge Steward Johnston & Reens LLC (57) ABSTRACT

A method for assembling an endoscope with a first tubular channel for receiving image-transmitting components and with a second channel for receiving light guides. It is proposed to introduce the light guides first into a flexible tube and to introduce the unit made up of flexible tube and light guides into the second channel.

14 Claims, 4 Drawing Sheets

U.S. PATENT DOCUMENTS

| | | | |
|---|---|---|---|
| 5,460,781 A * | 10/1995 | Hori et al. | 422/99 |
| 5,662,817 A | 9/1997 | Honmou | 216/24 |
| 6,337,737 B1 * | 1/2002 | Chang et al. | 356/32 |
| 2001/0012429 A1 * | 8/2001 | Wach et al. | 385/115 |
| 2003/0045780 A1 * | 3/2003 | Utsui | 600/182 |

FOREIGN PATENT DOCUMENTS

| | | |
|---|---|---|
| DE | 37 38 451 | 5/1988 |
| DE | 38 22 885 | 1/1989 |
| DE | 42 07 092 | 9/1993 |
| EP | 0 459 415 | 12/1991 |
| EP | 1 271 213 | 1/2003 |
| GB | 1 463 350 | 2/1977 |
| JP | 9 127379 | 5/1997 |

* cited by examiner

METHOD FOR ASSEMBLING AN ENDOSCOPE

This application is a continuation of pending international application PCT/EP2004/000766 filed on Jan. 29, 2004 which designates US and which claims priority of German patent application No. 103 07 903.3 filed on Feb. 18, 2003.

BACKGROUND OF THE INVENTION

The invention relates to a method for assembling an endoscope with a first tubular channel for receiving image-transmitting components, and with a second channel for receiving light guides.

The invention likewise relates to such an endoscope.

Endoscopes have become widely used in the medical sector and have opened up the possibility of what is referred to as minimally invasive surgery. In the meantime, a further area of use has been in the field of so-called "industrial endoscopy" in which the endoscopes are used for visual inspection of hollow spaces, for example in engines, vehicle bodyworks, aircraft turbines, buildings, etc.

Such endoscopes have a first tubular channel for receiving image-transmitting elements. These image-transmitting elements are elements of an optical system, such as lenses, in particular rod lenses, spacers, diaphragms, prisms, filters or the like. These transmit the image in the direction from distal to proximal. In electronic image-processing, a miniature camera in the form of a CCD chip is used which converts the optical signals into electrical signals.

The light needed for viewing purposes is provided by light guides which conduct the light from a light source in the proximal to distal direction. These light guides are usually formed by a bundle of glass fibers.

When assembling the endoscope, the light guides are introduced in the form of a bundle of glass fibers directly into a second channel, and the latter is then closed at both ends. This second channel is formed by a second tube being pushed over the first tubular channel and then surrounding the latter so that a gap between the first tubular channel and the second tube forms the second channel as a channel having the cross section of a continuous ring or with a crescent-shaped and if appropriate non-continuous cross section. Such endoscopes have an elongate shaft in which the two channels for receiving the image-transmitting and light-conducting components are provided. At the proximal end, the shaft opens into an endoscope housing whose proximal end, depending on its design, in turn has an eyepiece cup or an attachment for a camera module. By virtue of the flexibility of the thin light guides made of glass fibers, it is possible to route these to a light guide attachment protruding transversely with respect to the longitudinal axis of the shaft. In a fully assembled endoscope, a first elongate portion of the light guide extends along the shaft axis in the second channel and is then angled to the side at about 90° in the housing via a corresponding bend or curve in the direction of the light guide attachment.

The shaft of such an endoscope is usually composed of an outer tube in which an inner tube is received in whose interior the first channel is formed and which serves to receive the image-transmitting elements. If the inner tube is arranged coaxially with respect to the outer tube, a hollow cylindrical space is formed between the outside face of the inner tube and the inside face of the outer tube, and this space forms the second channel for receiving the light guides in the shaft area.

If the inner tube is arranged laterally offset in the outer tube, in most cases such that it bears along an outer surface line on an inner surface line of the inside face of the outer tube, then a crescent-shaped space is obtained which represents the second channel for receiving the light guides.

It has been found that assembly of the light guide in the form of a loose bundle of glass fibers requires a certain amount of practice and considerable dexterity. However, it is difficult to avoid some of the glass fibers breaking during assembly, in which case they cannot be used to conduct light. It has also been found that, after a large number of sterilization cycles, moisture or other forms of contamination can penetrate into the second channel and adversely affect the quality of light conduction.

The glass fiber bundle is fixed at the distal and proximal ends by adhesive bonding. Creep of the adhesive along the glass fibers and away from the fixing locations has been noted, which leads to undesired adhesion of individual glass fibers to one another and undesired adhesion of glass fibers to the inner or outer tube away from the fixing locations at the ends. In the event of thermal and mechanical expansion stresses and shocks, this leads to fracturing of glass fibers, and these can then no longer serve for light conduction.

It is an object of the present invention is to remedy this situation and make available a method and an endoscope of the type mentioned at the outset which is easy to assemble and which ensures lasting and excellent light conduction.

SUMMARY OF THE INVENTION

According to the invention, the object is achieved by the light guides being introduced into a flexible tube, and by the unit composed of tube and light guides being introduced into the second channel.

By means of this preliminary assembly step, it is now possible to introduce the light guides, if appropriate using assembly aids, into a flexible tube. This insertion or introduction into the flexible tube is possible without breaking individual light guides. This unit is then introduced into the second channel of the endoscope, which is much easier to do than would be the case with a loose bundle of light guides. The flexible tube also effects the curving or bending of the bundle of light guides received in the tube for the purpose of bringing the unit to the laterally angled light guide attachment or engaging it in the latter. By manipulation of the outer tube enclosing the inner glass fibers, it is then possible to correct the position by forward and backward movements, without this manipulation posing any risk of individual fibers twisting or even breaking and then being no longer usable for light conduction.

The flexible tube additionally protects the light guide fibers, during subsequent use of the endoscope, from radial penetration of moisture or contamination, so that not only is assembly made easier, the operational reliability is improved and the lifetime of the light guide elements is increased. Particularly in the area of curvature, that is to say the area where the guides are routed proximally from the longitudinal extent of the shaft to the lateral light guide attachment, these light guides are now especially protected, with the result that they cannot be damaged by other components in the housing of the endoscope. Even if some parts come loose or move inside the endoscope because of sudden jolts or the like, these parts cannot directly impact the bundle of light guides since this bundle is protected, in the critical area, by the surrounding flexible tube. In revision work or repairs, it is thus also possible to use tools for manoeuvres in the area of the housing, without there being any risk of affecting exposed areas of the sensitive light guides in the form of glass fibers.

In one embodiment of the invention, the light guides have such a length that they protrude from both ends of the tube.

This measure has the advantage that the two protruding ends can be used for fixing as usual at the respective proximal or distal end, for example by suitable adhesive bonds. These adhesive bonds are produced in such a way that the ends of the light guides are fixed in position and, at the same time, the adhesive forms a tight seal at the proximal end and at the distal end of the endoscope or of the light-conducting path.

This measure has the advantage that the bundle of light guides is positionally fixed and sealed at these end locations, but axial expansions are possible between these areas in the sterilization cycles which are carried out at elevated temperatures (up to ca. 170° C.), in general by autoclaving. The tube enclosing the light guide fibers between the fixing locations at both ends protects these sensitive light guide fibers, but nevertheless permits the expansion movements under fluctuating temperatures along the entire expansion length between the proximal end area and the distal end area.

In a further embodiment of the invention, the light guides are fixed in the tube.

This measure has the advantage that the light guides are positionally fixed in the area of the tube, but expansion movements for stress compensation are possible because of the flexibility.

In a further embodiment of the invention, the light guides are fixed in the area of the tube ends.

This measure has the advantage that a defined position of the light guides in the area of the ends of the tube is ensured by the fixing, while in the area between these ends there is still sufficient freedom of movement to permit expansions upon temperature fluctuations or bending or curving to guide the light guides. The fixing also ensures that, upon manipulation during assembly, the ends of some of the light guide fibers are not inadvertently drawn into the tube and caught there. Their ends then no longer reach to the distal or proximal end face and these light guides can thus no longer be used for light conduction.

In a further embodiment of the invention, the light guides are fixed in the tube by an adhesive.

This measure has the advantage that, if so required, the light guides can be fixed not only at the ends but also along the length of the tube. This can be done along partial areas, along several partial areas or the like, in order to permit the aforementioned temperature stress expansions as before.

In a further embodiment of the invention, the adhesive bonds are produced in such a way that the light guides are fixed sealingly in the area of the tube ends.

This measure has the advantage that these fixing locations at the same time serve as seals, so that it is possible to exclude the possibility of any contamination, in particular vapor or the like, getting into the interior of the tube.

In a further embodiment of the invention, in the case of a hollow cylindrical second channel, several tubes enclosing the light guide fibers are distributed around the circumference.

This measure has the advantage that, in this spatial configuration, several lines of tubes, with light-conducting fibers contained in them, can be fitted.

This can be done particularly advantageously if about four tubes are fitted at 90° with respect to one another around the circumference.

In a further embodiment of the invention, in the case of a hollow cylindrical second channel, a unit composed of tube and light guides is produced which has a central core.

This measure has the advantage of creating a possibility of uniformly filling the entire hollow cylindrical second channel with light guides. The central core is in this case chosen such that its dimensions correspond to the later inner tube of the endoscope. It is thus possible, outside the endoscope, to distribute the individual light guide fibers in a suitably uniformly distributed form in the cavity between the central core and the outer tube and, if appropriate, also to fix them, and then to push this unit from the core directly into the endoscope. In this case, the core can be fitted onto the inner tube, and the unit can be removed from the core and pushed onto the inner tube.

In an advantageous embodiment, the light guides are coated with an adhesive and the adhesive is cured while the core is still inserted.

This measure has the advantage that the adhesive fixes the light guides in the geometrical arrangement of the hollow cylindrical body. This preliminary curing and the fact that light guide fibers are optionally firmly connected or bonded along their entire length to the tube means that, upon thermal expansion, which markedly differs between the light guide fibers and the endoscope shaft, the tube may be damaged or tear because of the light guide fibers being subjected to stress. In order to prevent possible loss of leaktightness from outside with respect to the bundle of fibers, a further tube can if appropriate be provided around the tube directly surrounding the bundle of fibers.

In a further embodiment, a tube is also arranged over the core.

This measure has the advantage that a hollow cylindrical structure is pre-formed which, both on the inner and on the outer cylindrical wall, has a tube between which the light guide fibers are received.

In a further embodiment of the invention, the tube is first provided as a rectangular strip onto which the light guides are placed, and the strip is then closed around the light guides to form a tube.

This measure has the advantage that in the case of extreme geometric configurations, for example in the case of extremely long and thin endoscopes, only a very slight clear diameter of the second channel is available, and this could cause some difficulty in introducing the light guide bundles into such a thin and possibly also long channel. The unit thus formed is then handled in the manner already described.

In a further embodiment of the invention, an insertion aid widened in a funnel shape is fitted into one end of the tube during assembly, and the light guides are pushed into the tube via this insertion aid, after which the insertion aid is removed.

This measure has the advantage that inserting the light guide bundle into the tube is greatly simplified. The tube can be arranged in a suspended position, and the insertion aid can be inserted into the upper end of the tube and the light guide fibers then pushed in gently from above.

In a further embodiment of the invention, a tube is used which is made of shrinkable material.

This measure has the advantage that, after introduction of the light guides, the material of the tube can be shrunk so that the light guides are additionally fixed.

In a further embodiment of the invention, the tube is shrunk after introduction into the second channel.

In the case of the aforementioned crescent-shaped second channel for example, this measure has the advantage that the tube is first pushed in as a loose structure into such a form, and it is then adapted and afterwards fixed by the shrinking process to adapt to this geometry.

In a further embodiment of the invention, the tube is shrunk before introduction into the second channel.

This measure is of advantage if, for example, simple geometries are present and it is desired to fix the unit before insertion, for example into a hollow cylindrical channel. This also opens up the possibility of originally providing a tube of relatively large diameter, into which the bundle of light guide fibers is introduced and positioned with radial clearance, if appropriate using an insertion aid, and can then be fixed by shrinking. The unit, which is flexible as before, can then be used correspondingly. This also permits a stock of such units to be kept which are then removed from a stock and used at the time of actual assembly.

In this connection, it should be noted in particular that both the curing of adhesive located between light guide fibers, or between light guide fibers and the inner or outer tube, and the shrinkage of the tubes around the light guide fibers can take place before introduction into the endoscope shaft and also thereafter. In the former case, it is possible, before curing/shrinking, to pre-model the form of the for example tube-shaped bundle later to be introduced in the cured/shrunk state.

It is also possible to pre-shrink the tube before introduction into the second channel and then to shrink it again after introduction.

In a further embodiment of the invention, the curing of the adhesive and the shrinking of the tube take place simultaneously under the action of heat.

This measure has the advantage of straightforward and energy-saving production in which both the tube is shrunk and the adhesive also cured, so that a suitably prefabricated unit can be produced by means of a single heat treatment operation.

It will be appreciated that the features mentioned above and those still to be explained below can be used not only in the respectively cited combinations, but also in other combinations or singly, without departing from the scope of the present invention.

BRIEF DESCRIPTION OF THE DRAWINGS

The invention is described and explained in greater detail below on the basis of a number of selected illustrative embodiments and with reference to the attached drawings, in which.

DETAILED DESCRIPTION OF PREFERRED EMBODIMENTS

Figure 1:
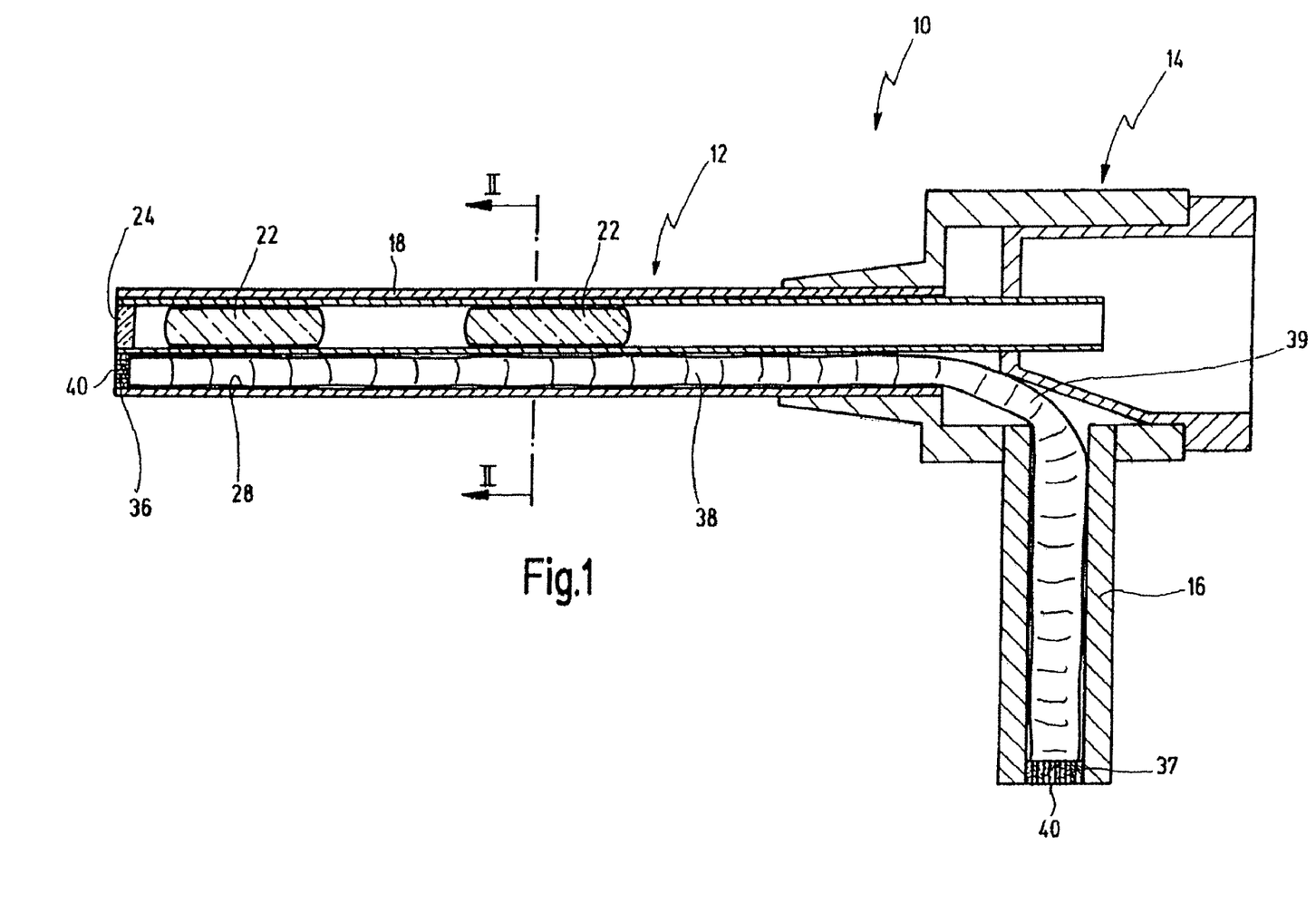
FIG. 1 shows a highly schematic longitudinal section through an endoscope during assembly, with a unit made up of flexible tube and light guides already inserted into the second channel.

An endoscope shown in FIG. 1 is designated overall by reference number 10.

The endoscope 10 has an elongate shaft 12 which is provided at the proximal end with a housing 14.

A light guide attachment 16 extends laterally from the housing 14, at an angle of approximately 90° with respect to the longitudinal axis of the shaft 12. In the area of its housing 14, the endoscope 10 is shown in the state before its final assembly, and, for the sake of clarity, the optical elements contained in the housing 14 and the eyepiece cup at the end are not shown.

Figure 2:
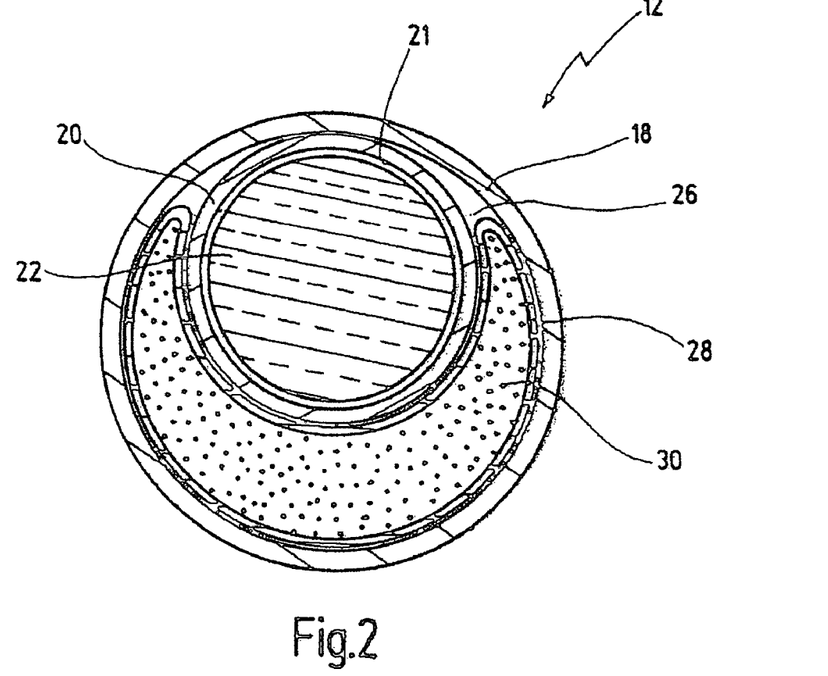
FIG. 2 shows a cross section along the line II-II in FIG. 1.

The shaft 12 of the endoscope 10, as will also be seen from the sectional representation in FIG. 2, is composed of an outer tube 18 in which an inner tube 20 of smaller diameter is received. The inner tube 20 is arranged eccentrically, i.e. it bears along an outer surface line on an inside face of the outer tube 18, as will be seen in particular from the sectional representation in FIG. 2.

The interior of the inner tube 20 represents a first tubular channel 21 for receiving the image-transmitting elements of the endoscope 10.

FIG. 1 shows only some of these image-transmitting elements by way of example, namely two rod lenses 22 and a closure window 24 closing the first tubular channel 21 at the proximal end. Between the outside of the inner tube 20 and the inside of the outer tube 18 there is a second channel 26 which, in the area of the shaft 12, has a crescent-shaped cross section, as can be seen in particular from FIG. 2.

The crescent-shaped second channel 26 accommodates a unit 38 made up of a flexible tube 28 and, contained in the latter, light guides 30 in the form of a bundle of glass fibers. The structure of the unit 38 will first be described in greater detail with reference to FIG. 3.

Figure 3:
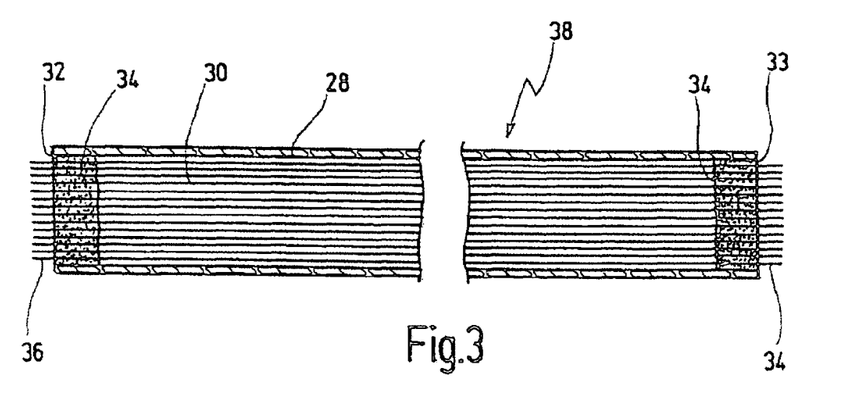
FIG. 3 shows a preliminary assembly state, specifically the unit made up of flexible tube and light guides which is fitted in the endoscope in FIG. 1.

As has been mentioned, the unit 38 is composed of a flexible tube 28 of plastic material. In the illustrative embodiment shown, the material is a shrinkable plastic material.

A bundle of glass fibers is inserted into the flexible tube 28, the length of said bundle being chosen such that the opposite ends 32 and 33 protrude slightly, by approximately 1 cm the flexible tube 28. The bundle of glass fibers represents the light guide 30. In the area of the ends 32 and 33, the glass fibers are connected to one another, and also to the inside of the flexible tube 28, by an adhesive 34. The adhesive 34 is chosen and applied in such a way that a tight seal is ensured, so that no contamination such as moisture or superheated steam can get into the interior of the flexible tube 28 from the outside.

To introduce the light guides 30 into the flexible tube 28, the latter can be suspended vertically, and an insertion aid, widened outward in a funnel shape, can be fitted into one end, namely into the upper end, for example the end 33. The light guides 30 are introduced from above as a glass fiber bundle downward via the insertion aid. To do this, the glass fibers are moistened slightly with a moistening agent which can be easily vaporized, as a result of which they are held together by adhesion forces in a coherent, approximately rod-shaped bundle. After the light guides 30 have been introduced, the adhesive 34 is introduced into the area of the ends 32 and 33 and cured, if appropriate, with the aid of heat. A possible shrinking of the flexible tube 28 of shrinkable material is taken into account in this curing in the area of the ends 32 and 33.

The unit 38 shown in FIG. 3 is now introduced, e.g. pushed, into the second channel 26 of the endoscope 10, specifically in the direction from distal to proximal, that is to say from left to right in the view in FIG. 1. The unit 38 can be pushed in in a completely straight orientation, or can be twisted in, so that it protrudes from the proximal end of the still open housing 14. In this state of assembly, the lateral light guide attachment 16 is not yet fitted into the housing 14. By gently bending the unit 38, the latter is angled sideward and pushed out of the corresponding opening into which the light guide attachment 16 is twisted. The light guide attachment 16 is then pushed on over this laterally suspended end of the unit 38 and inserted. The circumference of the flexible tube 28 is chosen such that it can fit snugly against the crescent-shaped cross-sectional contour of the second channel 26, as is evident in particular from the sectional view in FIG. 2. In this way, the individual glass fibers of the bundle, which together represent the light guide 30, are then distributed uniformly in the crescent-shaped area.

The tube 28 with circular cross section is routed away via the lateral light guide attachment 16.

It will be seen from FIG. 1 that, in the curved transition area 39, the light guides 30 are protected by the flexible tube 28. In this state of assembly, the tube can now be shrunk, and a procedure can then be performed in which adhesive 40 is first applied to the protruding ends 36 and 37 and these are bonded to form a tight closure plug which, at the distal end, then has the cross-sectional shape of a crescent moon within the dimensions of the second channel 26 and, at the proximal and laterally angled end, has the cross-sectional shape of the clear internal diameter of the light guide attachment 16. However, it is also possible for the tube 28 to be shrunk only at this stage, and this can be done by a common heat treatment which is used to cure the adhesive 40 and at the same time to effect shrinking.

The light guides 30 in the interior of the tube 28 are protected all round and are secured only via the proximal and distal adhesion points at the ends. This permits certain movements, particularly thermal expansion movements during the sterilization cycles, if the endoscope 10 is used for the medical sector. If it is used in the industrial sector, it can also compensate for the corresponding thermal expansion stresses, for example if it is used in a warm or hot space.

The material and the geometry of the flexible tube 28 can be chosen such that, by means of the shrinking process, it is possible to form different sites of fixing to the inside wall of the second channel 26 or of the light guide attachment 16. For this purpose, the material of the tube 28 can be provided, for example, with beads or bulges which, upon radial contraction during shrinkage, ensure a certain axial attachment to the walls surrounding the flexible tube 28.

Figure 4:
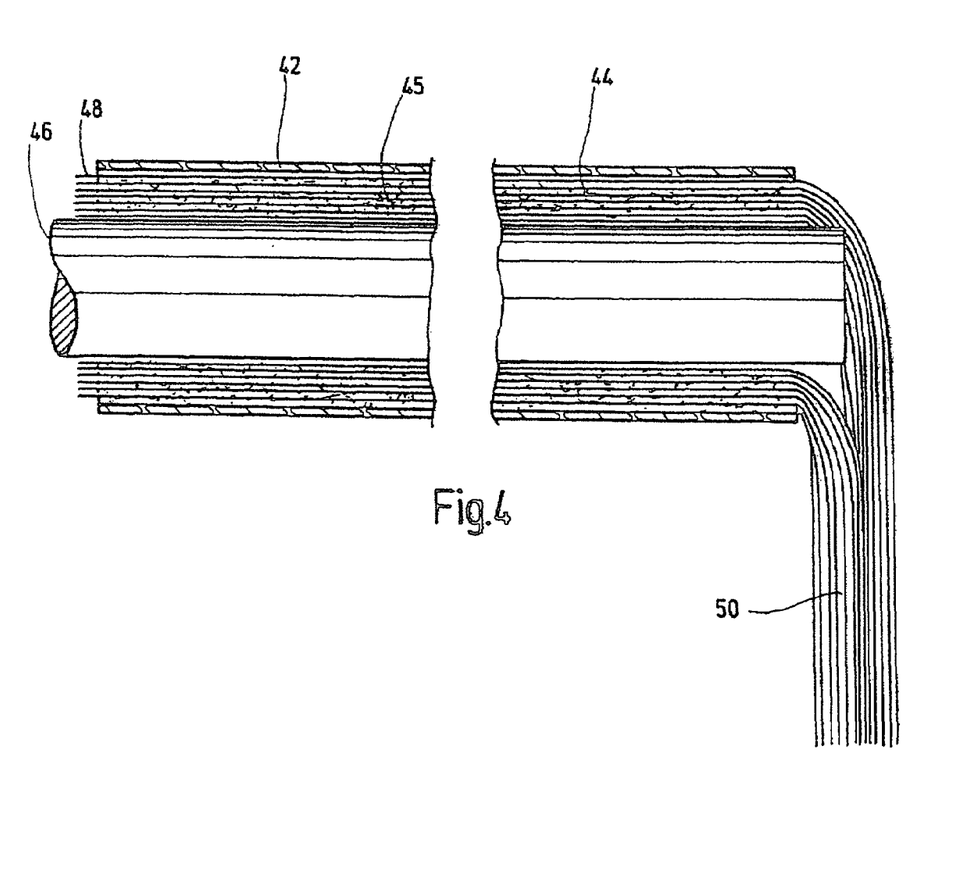
FIG. 4 shows a representation comparable to the representation in FIG. 3 and showing a preliminary assembly unit made up of flexible tube and light guides for an endoscope with a hollow cylindrical second channel.

In the illustrative embodiment shown in FIG. 4, a flexible tube 42 is provided, into whose interior light guides 44 are introduced, said light guides 44 in this case too being composed of a bundle of fine light-conducting glass fibers. The light guides 44 have been wetted beforehand along their entire length with an adhesive 45. A core 46 is driven in centrally, said core possibly having a point to facilitate its insertion. The length of the light guides 44 is chosen such that they protrude slightly, by approximately 1 cm, from one end, which will later be the distal end, while at the opposite end they have a longer exposed portion 50. After curing of the adhesive 45, a light guide structure is obtained, around the core 46, in the form of a hollow cylinder, as can be seen from the cross section in FIG. 5.

Figure 5:
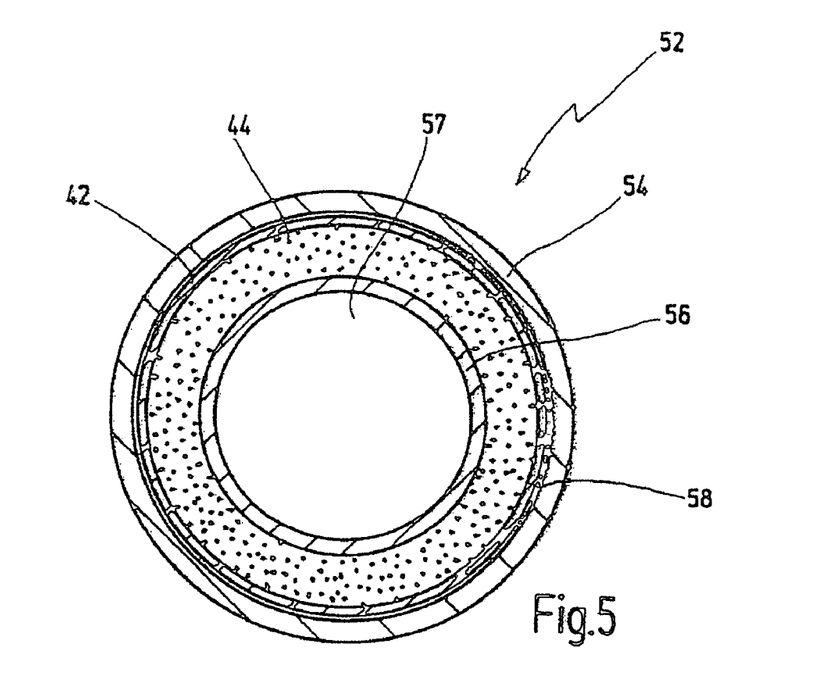
FIG. 5 shows a section, comparable to the one in FIG. 2, showing an endoscope shaft in which a unit as shown in FIG. 4 has been fitted.

The shaft 52 of an endoscope shown in this figure has an outer tube 54, in which an inner tube 56 is received concentrically. The interior of the inner tube 56 here once again delimits a first channel 57 provided for receiving the image-transmitting system, that is to say, for example, the above-described lenses, etc.

The space of annular cross section around the outside of the inner tube 56 and the inside of the outer tube 54 represents the second channel 58 for receiving the light-conducting system.

The core 46 therefore has an external diameter which corresponds approximately to the external diameter of the inner tube 56. Upon assembly, the unit shown in FIG. 4 can now be pushed through the housing of the endoscope, for example from the proximal direction, and applied in such a way that the core 46 is approximately in alignment with the inner tube 56. The unit made up of light guides 44 and flexible tube 42 can now be pushed directly off from the core 46 and pushed into the second channel 58. The exposed portion 50 can then be pushed into the lateral light guide attachment; a suitable tube can also be pushed over it beforehand. It is also possible to push a further tube over the outside of the shaft 52 so that the hollow cylindrical unit then has a suitable flexible tube both on the inside and also on the outside. Here too, the protruding distal ends 48 of the glass fibers are used for adhesion to form a tight closure with the distal end of the endoscope, as has been described above in the discussion of FIG. 1. Here too, provision is made for the flexible tube 42 to be made of shrinkable material, and for the unit to be shrunk to form a compact unit before insertion into the endoscope.

Figure 6:
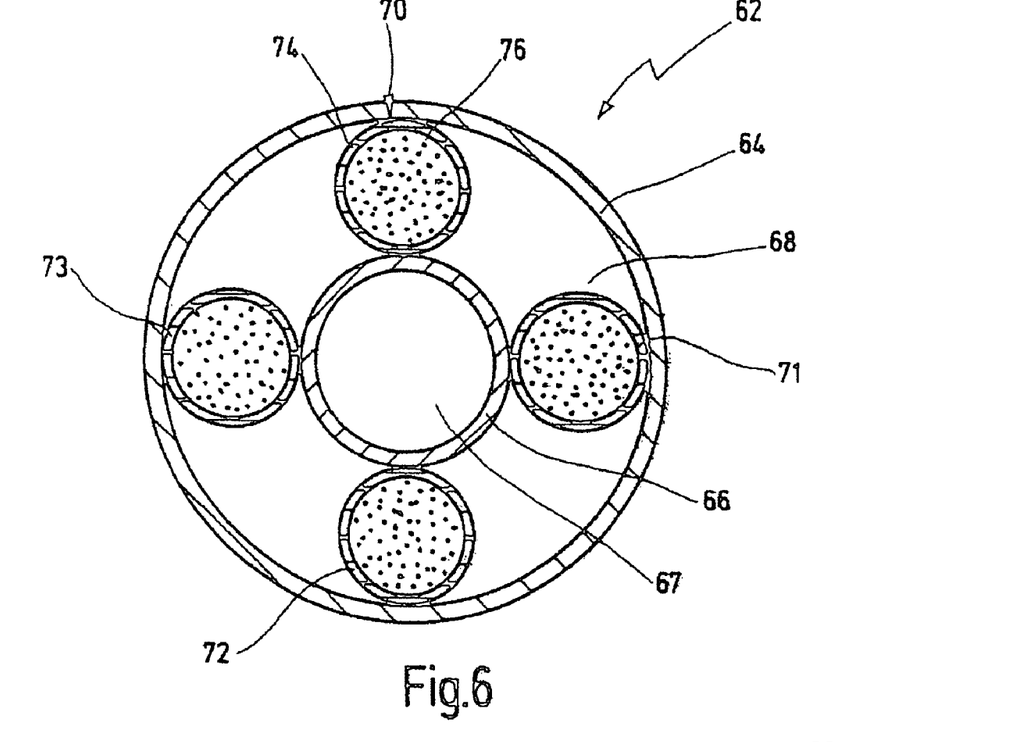
FIG. 6 shows a section, comparable to the representation in FIG. 5, of an endoscope with a hollow cylindrical second channel in which four flexible tubes, with light guides contained in them, are distributed about the circumference.

FIG. 6 shows a cross section of a shaft 62 which, similarly to what has been described above, is composed of an outer tube 64 and of an inner tube 66 arranged concentrically with respect to the latter. The inner tube 66 again delimits the first channel 67 for receiving the image-transmitting system. Here too, there is once again a second channel 68 which is delimited by the outside of the inner tube 66 and by the inside of the outer tube 64 and is of a hollow cylindrical shape. It will be seen from FIG. 6 that four units 70, 71, 72, 73, as described before in FIG. 3, are now pushed into this hollow cylindrical second channel 68. These units are in this case arranged such that they are offset by 90° relative to one another. Each individual unit (only the unit 70 is discussed here as a representative example) is once again composed of a flexible tube 74 in whose interior there is a light guide 76 made up of a bundle of fine glass fibers. Retention can be obtained mechanically, namely by the spacers which hold the inner tube 66 in coaxial alignment with the outer tube 64. These spacers consist of at least two, possibly more, axially spaced rings which are pushed onto the inner tube 66 and have four through-openings which are offset by 90° relative to one another and through which the units 70, 71, 72, 73 are pushed.

It will be seen from the sectional view in FIG. 6 that other channel-like openings are left free between the individual units and these are used to receive further channels or lines, for example irrigation channels for irrigation fluids, or suction channels for suctioning of fluids or gases.

Figure 7:
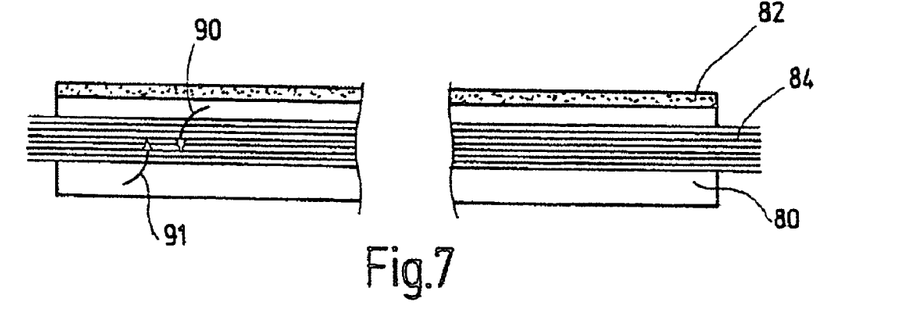
FIG. 7 shows a plan view of a preliminary assembly state of a unit made up of a rectangular strip and light guides, the rectangular strip being intended to be rolled up to form a tube.
Figure 8:
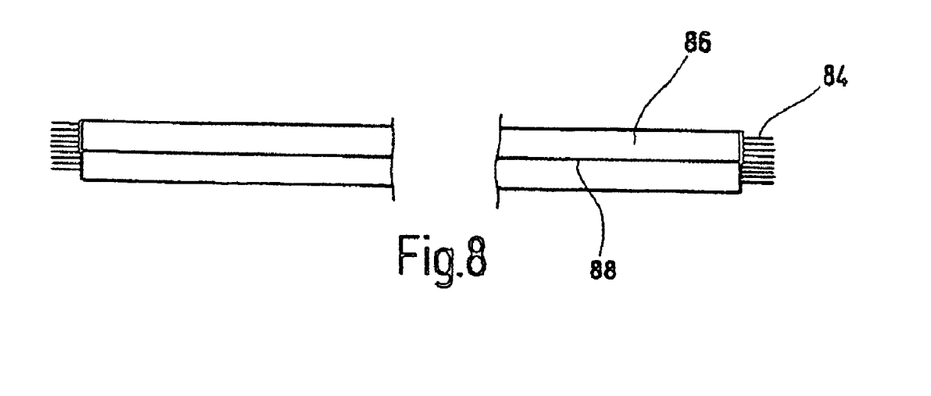
FIG. 8 shows a representation comparable to FIG. 7, after the rectangular strip has been formed into a tube.

FIGS. 7 and 8 show how an above-described unit composed of tube and light guides can be produced if an extremely long and thin endoscope is present. In this case, it may sometimes be difficult to safely introduce the light guides into an interior of a tube.

For this purpose, a suitable rectangular strip 80 is used which is provided with an adhesive edge 82 along one long side. The light guide 44, that is to say a bundle of glass fibers, is placed onto the strip 80, and the strip 80 is then shaped into a tube, one end first being folded over, as is indicated by an arrow 89, and the other end then being folded over so as to overlap this, as is indicated by an arrow 90, as a result of which the adhesive edge 82 fixes it in the form of a tube-shaped body.

This unit then of course has a seam 88, but this is not problematic in the case of a suitably thin tube material.

What is claimed is:

1. A method for assembling an endoscope, having
 a first tubular channel for receiving image transmitting components and a second channel for receiving light guides, said method comprising the steps of introducing said light guides into a flexible tube thereby forming a unit made up of said tube and said light guides received therein, and introducing said unit into said second channel, wherein said flexible tube is made of a shrinkable material and shrunk after introduction of said unit into said second channel.

2. The method of claim 1, wherein said light guides are provided with such a length that they protrude both ends of said flexible tube.

3. The method of claim 1, wherein said light guides introduced into said flexible tube are fixed in said flexible tube.

4. The method of claim 3, wherein said light guides are fixed in said flexible tube in opposed end areas of said tube.

5. The method of claim 3, wherein said light guides are fixed in said flexible tube by an adhesive.

6. The method of claim 5, wherein said fixing by an adhesive is made in such a manner, that said light guides are fixed sealingly in the area of ends of said flexible tube.

7. The method of claim 1, wherein said second channel is a hollow cylindrical channel surrounding said first tubular channel, a plurality of said units are distributed around a circumference of said hollow cylindrical second channel.

8. The method of claim 7, wherein four units, each offset by about 90° around said circumference, are distributed in said hollow cylindrical channel.

9. The method of claim 1, wherein said flexible tube is first provided as a rectangular strip, onto which said light guides are placed, and said strip is then closed around the light guides to form said flexible tube.

10. The method of claim 1, wherein a funnel is fitted into one end of the flexible tube serving as an insertion aid widened in shape, said light guides are inserted into said flexible tube via said insertion aid, and after inserting said light guides said insertion aid is removed.

11. A method for assembling an endoscope, having a first tubular channel for receiving image transmitting components and a second channel for receiving light guides, said method comprising the steps of introducing said light guides into a flexible tube thereby forming a unit made up of said tube and said light guides received therein, and introducing said unit into said second channel, wherein said flexible tube is made of a shrinkable material and is preshrunk before introducing said unit into said second channel and shrunk after introduction of said unit into said second channel.

12. A method for assembling an endoscope, having a first tubular channel for receiving image transmitting components and a second channel for receiving light guides, said method comprising the steps of introducing said light guides into a flexible tube thereby forming a unit made up of said tube and said light guides received therein, and introducing said unit into said second channel, wherein said second channel is designed as a hollow cylindrical channel surrounding said first tubular channel, said unit made up of said flexible tube and said light guides is produced having a central core corresponding to the diameter of the first tubular channel and wherein said light guides are coated with an adhesive, and said adhesive is cured with said core still inserted.

13. The method of claim 12, wherein a further tube is fitted over said central core.

14. A method for assembling an endoscope, having a first tubular channel for receiving image transmitting components and a second channel for receiving light guides, said method comprising the steps of introducing said light guides into a flexible tube thereby forming a unit made up of said tube and said light guides received therein, and introducing said unit into said second channel, wherein said light guides are fixed within said flexible tube via an adhesive, and said flexible tube is made of a shrinkable material, a curing of said adhesive and a shrinking of said flexible tube are carried out simultaneously under applying of heat.

* * * * *